(12) United States Patent
Nakada et al.

(10) Patent No.: US 7,920,769 B2
(45) Date of Patent: Apr. 5, 2011

(54) OPTICAL ELEMENT, INTEGRATED OPTIC DEVICE AND OPTICAL INFORMATION TRANSMISSION SYSTEM

(75) Inventors: Masafumi Nakada, Tokyo (JP); Jun Akedo, Ibaraki (JP)

(73) Assignees: NEC Corporation, Tokyo (JP); National Institute of Advanced Industrial Science and Technology, Tokyo (JP)

( * ) Notice: Subject to any disclaimer, the term of this patent is extended or adjusted under 35 U.S.C. 154(b) by 191 days.

(21) Appl. No.: 12/087,865

(22) PCT Filed: Jan. 19, 2007

(86) PCT No.: PCT/JP2007/051215
§ 371 (c)(1),
(2), (4) Date: Oct. 15, 2008

(87) PCT Pub. No.: WO2007/083842
PCT Pub. Date: Jul. 26, 2007

(65) Prior Publication Data
US 2009/0310903 A1  Dec. 17, 2009

(30) Foreign Application Priority Data
Jan. 20, 2006  (JP) ................................. 2006-012346

(51) Int. Cl.
*G02B 6/10* (2006.01)
*G02F 1/295* (2006.01)

(52) U.S. Cl. .............................. 385/129; 385/8; 310/358
(58) Field of Classification Search ............... 385/8, 129
See application file for complete search history.

(56) References Cited

U.S. PATENT DOCUMENTS

| 7,120,326 B2 | 10/2006 | Nakada et al. | |
|---|---|---|---|
| 2003/0048042 A1* | 3/2003 | Yamaguchi et al. | 310/328 |
| 2004/0043230 A1* | 3/2004 | Hatono et al. | 428/458 |
| 2005/0147343 A1 | 7/2005 | Nakada et al. | |

FOREIGN PATENT DOCUMENTS

| JP | 62-7631 | 1/1987 |
|---|---|---|
| JP | 2-221382 | 9/1990 |
| JP | 2001-3180 | 1/2001 |
| JP | 2002-187767 | 7/2002 |
| JP | 2002-235181 | 8/2002 |
| JP | 2005-181995 | 7/2005 |
| WO | WO 03/100131 A1 | 4/2003 |

OTHER PUBLICATIONS

"Comparison of electro-optic lead-lanthanum zirconate titanate films on crystalline and glass substrates", K.D. Preston and G.H. Haertling, Appl. Phys. Lett. vol. 60, No. 23, Jun. 8, 1992, 2831-2833.

(Continued)

*Primary Examiner* — Hemang Sanghavi
(74) *Attorney, Agent, or Firm* — McGinn IP Law Group, PLLC (57) ABSTRACT

In a compact formed by subjecting an ultrafine particle brittle material supplied on a substrate to mechanical impact force as a load, whereby the ultrafine particle brittle material is crushed and joined to each other, manganese is added into the ultrafine particle brittle material to form the compact.

19 Claims, 3 Drawing Sheets

OTHER PUBLICATIONS

"Patterning of (Pb, La)(Zr, Ti) 03 waveguides for fabricating micro-optics using wet etching and solid-phase epitaxy", K. Nashimoto, K. Haga, M. Watanabe, S. Nakamura and E. Osakabe, Appl. Phys. Lett. vol. 75 No. 8, Aug. 23, 1999, 1054-1056.

"Ceramics thin film form technique using an impact consolidation phenomenon of minute particles and ultrafine particles-low-temperature and high-speed coating by means of an aerosol depostion method-" Jun Akedo and Maxim Lebedev, Materia, the forty-first volume, No. 7, 2002, 459-465.

"Microstructure and Electrical Properties of Lead Zirconate Titanate (Pb(Zr52/Ti48) Thick Films Deposited by Aerosol Deposition Method", Jun Akedo and Maxim Lebedev, Jpn. J. Appl. Phys. vol. 38 (1999), Pt. 1, No. 9B, 5397-5401.

"Optical and electro-optical properties of Pb(Zr,Ti)03 and (Pb, La)(Zr, Ti)03 films prepared by aerosol deposition method", Masafumi Nakada, Keishi Ohashi and Jun Akedo, Journal of Crystal Growth, 275 (2005), e1275-e1280.

* cited by examiner

OPTICAL ELEMENT, INTEGRATED OPTIC DEVICE AND OPTICAL INFORMATION TRANSMISSION SYSTEM

TECHNICAL FIELD

The present invention relates to an optical element used for optical communication, optical wiring or optical storage, an integrated optics device into which the optical elements are integrated, and an optical information transmission system using them.

BACKGROUND ART

A demand of an optical element constituting optical communication or optical storage has been increased with the spread of them. Particularly, in the optical communication, usage from a so-called backbone system centering on an optical fiber to a metro or access system is accelerated with practical application of wavelength multiplex transmission. For this reason, in the optical element used for add-drop and the like of an optical signal, usage of a small-sized and easily-integrated planar waveguide using a thin film of an optical material also proceeds in place of one in which a bulk material is combined.

In order to control light actively like modulation or switching of an optical signal, it is required to use a physics effect by interaction between an external input signal, such as electricity or heat, and a material that forms the optical element. In a silicon-system planar waveguide, an optical switch that uses a thermooptical effect by adding a heater to a directional coupler, a switch by combination of a MEMS (Micro Electric Mechanical System) and the like are known. However, both of them have a defect that response speed is slow in a μs (micro seconds) level. In addition, an optical switch using a thermooptical effect has a defect that power consumption is large while a switch of a MEMS type has a defect that a structure becomes complex and it is expensive.

An electro-optic element whose index of refraction is changed by interaction between an electric field and a substance is applied to an optical modulator because of its high speed, low power consumption due to driving with voltage, simplicity of its structure. In an optical modulator using $LiNbO_3$, a Mach-Zehnder type waveguide is formed on a single-crystal $LiNbO_3$ substrate by means of a Ti diffusion method, and it is combined with an electrode to form the optical modulator. Then, by applying voltage to the electrode, an index of refraction of the waveguide is changed, whereby ON/OFF of an optical signal can be carried out. However, since this optical modulator requires to use a single-crystal substrate, it becomes expensive. Further, since an electro-optical effect of $LiNbO_3$ is small, the waveguide is required to be lengthened. There is a defect that the element size is very large in cm order.

An electro-optical coefficient of $Pb_{1-x}La_x(Zr_yTi_{1-y})_{1-x/4}O_3$ (PLZT) that is transparent ceramics is almost double-digit larger than that of $LiNbO_3$ single crystal used in an existing optical modulator. Therefore, low cost, low power consumption and high speed can be expected by making the optical element smaller, and examination of a thin film by a sol-gel method has been made so far. For example, see "Comparison of electro-optic lead-lanthanum zirconate titanate films on crystalline and glass substrates", K. D. Preston and G. H. Haertling, Appl. Phys. Lett. Vol. 60, No. 23, 8 Jun. 1992, 2831-2833, and "Patterning of (Pb, La)(Zr, Ti)$O_3$ waveguides for fabricating micro-optics using wet etching and solid-phase epitaxy", K. Nashimoto, K. Haga, M. Watanabe, S. Nakamura and E. Osakabe, Appl. Phys. Lett. Vol. 75 No. 8, 23 Aug. 1999, 1054-1056.

However, in order to form a PLZT thin film having high optical transmittance and a large electro-optical effect, it is required to be epitaxially grown. Namely, a single-crystal substrate is required as a substrate material. Therefore, there has been a defect that it is expensive because it is difficult to form it on other substrate such as a silicon system waveguide and a prolonged period of film formation process is required to form a film thickness necessary for the optical element by a sol-gel method.

Each of optoelectronics materials such as $LiNbO_3$ and PLZT is a ferroelectric material, and its property is expressed in the case of forming a crystal structure particular to each compound. For this reason, in order to use an optoelectronics material as the optical element, it has been thought that its own single-crystal substrate is to be used or an optoelectronics material is epitaxially grown on the single-crystal substrate.

In future, realization of a nanophotonic device capable of integrating light and electronics on one chip is requested as a large innovative technology. In order to achieve this, a technique to form LSI, such as a CPU and a memory, and an active optical element, such as an optical switch, on the same substrate is required, and a technique to form a film of an optoelectronics material such as PLZT on a silicon or silica substrate with high crystallinity is requested.

On the other hand, as a new film formation technique of oxide, aerosol deposition (AD method) using a room temperature impact consolidation phenomenon has been developed. An AD method uses an impact adhesion phenomenon of an ultrafine particle material, and it is expected to achieve high film formation speed and low process temperature compared with a conventional thin film formation method. For example, see "Ceramics thin film form technique using an impact consolidation phenomenon of minute particles and ultrafine particles—low-temperature and high-speed coating by means of an aerosol deposition method—", Jun Akedo and Maxim Lebedev, *Materia*, the forty-first volume, No. 7, 2002, 459-465, and "Microstructure and Electrical Properties of Lead Zirconate Titanate ($Pb(Zr_{52}/Ti_{48})O_3$) Thick Films Deposited by Aerosol Deposition Method", Jun Akedo and Maxim Lebedev, Jpn. J. Appl. Phys. Vol. 38 (1999), Pt. 1, No. 9B, 5397-5401.

Further, since in the AD method a film property does not depend on a foundation layer, it is possible to select a substrate freely.

Japanese Patent Application Publication No. 2001-3180 discloses a low-temperature formation method of a brittle-material ultrafine particle compact using an AD method. In this method, an ultrafine particle brittle material supplied on a substrate is subjected to mechanical impact as a load, whereby the ultrafine particle brittle material is crushed and the ultrafine particle brittle materials are joined to each other or the ultrafine particle brittle materials are joined to the substrate and to each other. This achieves joining of mutual ultrafine particles, and the film with high density and high intensity is formed without applying heat.

Japanese Patent Application Publication No. 2002-235181 discloses a structure formed by an AD method. The structure is a polycrystal that has no crystal orientation, and is characterized in that there is substantially no grain boundary layer composed of a glass layer. Further, this structure is characterized in that an average crystallite diameter is 50 nm or less and compacity is 99% or more.

Examination related to formation of a thin film of an optoelectronics material having high transparency by using an AD method has been made. For example, see "Optical and electro-optical properties of Pb(Zr, Ti)O$_3$ and (Pb, La)(Zr, Ti)O$_3$ films prepared by aerosol deposition method", Masafumi Nakada, Keishi Ohashi and Jun Akedo, Journal of Crystal Growth, 275 (2005), e1275-e1280. This clarifies that transmission loss of an AD film, which is a basic characteristic of an optical element, is caused by Rayleigh scattering of minute particles forming a compact and non-compact minute particles whose indices of refraction are different from those of the minute particles forming the compact.

Japanese Patent Application Publication No. 2005-181995 discloses an optical element by an AD method, an integrated optics device, an optical information transmission system and a method of manufacturing the same. In this method, a compact is formed by an impact consolidation phenomenon in which an ultrafine particle brittle material supplied on a substrate is subjected to mechanical impact force as a load, and the ultrafine particle brittle material is crushed and joined to each other, whereby an optical element is obtained. This optical element includes a portion having an index of refraction different from that of main formation of the compact, such as a pore (hole) and a heterogenous phase, and is characterized in that there is a relationship between an average radius d (nm) of the portion and a wavelength $\lambda$ (nm) of light that propagates through the compact as $d^6/\lambda^4 < 4 \times 10^{-5}$ (nm$^2$).

Transmission loss of a thin film formed by an AD method is composed of two components, optical scattering and optical absorption. As described above, a property of transmission loss due to optical scattering of the thin film formed by the AD method and a reduction method were revealed, but a method of reducing the optical absorption remains unrevealed.

DISCLOSURE OF THE INVENTION

The present invention is made in consideration of the circumstances described above, and it is an object of the present invention to provide a compact by an AD method, by which optical absorption is eliminated and transparency is heightened, and to provide an optical element composed of the compact. Further, it is another object of the present invention to provide an integrated optics device using the optical element composed of the compact by the AD method, and to provide an optical information transmission system.

The present invention is made in consideration of the circumstances described above. In a compact by an AD method, which is a room temperature impact consolidation phenomenon, optical absorption that does not occur in a bulk material occurs, and the present invention is made on the basis of discovery that it is effective to add manganese in order to reduce the optical absorption. This makes it possible to obtain a transparent compact by an impact consolidation method.

An optical element according to a first aspect of the present invention is an optical element including a compact, the compact being formed by subjecting an ultrafine particle brittle material supplied on a substrate to mechanical impact force as a load, whereby the ultrafine particle brittle material is crushed and joined to each other, wherein manganese is added into the ultrafine particle brittle material. This is based on discovery that optical absorption of the compact formed by the room temperature impact consolidation phenomenon is about 10%, but it can be reduced to nearly 0% by adding manganese thereto.

An optical element according to a second aspect of the present invention is an optical element including a compact, the compact being formed by means of a room temperature impact consolidation phenomenon by subjecting an ultrafine particle brittle material supplied on a substrate to mechanical impact force as a load, whereby the ultrafine particle brittle material is crushed and joined to each other, wherein manganese is added into the ultrafine particle brittle material, and an average radius d (nm) in a portion (pore (hole), heterogenous phase and the like) contained in the compact and having an index of refraction different from that of a main formation of the compact and a wavelength $\lambda$ (nm) of light that propagates through the compact have a relationship of $d^6/\lambda^4 < 4 \times 10^{-5}$ (nm$^2$).

Transparency of the compact formed by the room temperature impact consolidation phenomenon is defined by Rayleigh scattering and optical absorption. The optical absorption can be controlled by addition of manganese according to the first aspect. Rayleigh scattering occurs in the case where a size of a scatterer is sufficiently smaller than a wavelength of light. The size of the scattering can be defined by the wavelength and a radius of the scatterer. By setting a relationship between an average radius d (nm) and a wavelength $\lambda$ (nm) of light that propagates through the compact to $d^6/\lambda^4 < 4 \times 10^{-5}$ (nm$^2$), a scattering center radius of light can be made smaller than the wavelength of the light. Therefore, a transparent optical element can be obtained by the room temperature impact consolidation phenomenon.

An optical element according to a third aspect of the present invention is an optical element including a compact, the compact being formed by subjecting an ultrafine particle brittle material supplied on a substrate to mechanical impact force as a load, whereby the ultrafine particle brittle material is crushed and joined to each other, wherein manganese is added into the ultrafine particle brittle material, and an average radius d (nm) in a portion (pore (hole), heterogenous phase and the like) contained in the compact and having an index of refraction different from that of a main formation of the compact and a wavelength $\lambda$ (nm) of light that propagates through the compact have a relationship of $d^6/\lambda^4 < 1 \times 10^{-5}$ (nm$^2$).

By setting a relationship between the average radius d (nm) and the wavelength $\lambda$ (nm) of light that propagates through the compact to $d^6/\lambda^4 < 1 \times 10^{-5}$ (nm$^2$), it can make a scattering center radius of light sufficiently smaller than the wavelength of the light. Therefore, an optical element having further high transparency can be obtained by a room temperature impact consolidation phenomenon.

An optical element according to a fourth aspect of the present invention is the optical element in any one of the first to third aspects wherein the optical element is constructed from a lower electrode formed on the substrate, a waveguide formed on the lower electrode and made of the compact, and an upper electrode formed on the waveguide.

In this optical element, the waveguide is formed on the lower electrode. By forming the lower electrode using the room temperature impact consolidation phenomenon, a property of the waveguide does not depend on the kind of material of the lower electrode and a structure thereof. Therefore, it is possible to select a lower electrode freely, and an optimal optical design can be made.

An integrated optics device according to a fifth aspect of the present invention is an integrated optics device in which an optical element including a compact and at least one of optical elements, such as a laser, an electrical-optical converter, an optical-electrical converter, an optical amplifier, an optical waveguide, an optical filter or the like, are integrated on a substrate, the compact being formed by subjecting an ultrafine particle brittle material supplied on the substrate to mechanical impact force as a load, whereby the ultrafine particle brittle material is crushed and joined to each other, wherein manganese is added into the ultrafine particle brittle material, and an average radius d (nm) in a portion (pore (hole), heterogenous phase and the like) contained in the compact and having an index of refraction different from that of a main formation of the compact and a wavelength λ (nm) of light that propagates through the compact have a relationship of $d^6/\lambda^4 < 4 \times 10^{-5}$ ($nm^2$).

Integration of a plurality of optical elements, which is difficult because a manufacturing process is varied, is made possible by being formed by means of the impact consolidation phenomenon, in which it can be formed at room temperature even on any substrate material.

An integrated optics device according to a sixth aspect of the present invention is an integrated optics device in which an optical element including a compact and at least one of electronic circuits, such as a CPU, a memory or the like, are integrated on the same substrate, the compact being formed by subjecting an ultrafine particle brittle material supplied on the substrate to mechanical impact force as a load, whereby the ultrafine particle brittle material is crushed and joined to each other, wherein manganese is added into the ultrafine particle brittle material, and an average radius d (nm) in a portion (pore (hole), heterogenous phase and the like) contained in the compact and having an index of refraction different from that of a main formation of the compact and a wavelength λ (nm) of light that propagates through the compact have a relationship of $d^6/\lambda^4 < 4 \times 10^{-5}$ ($nm^2$).

Integration of an optical element and an electronic circuit on the same substrate, which is difficult because a manufacturing process is varied, is made possible by being formed by means of the impact consolidation phenomenon, in which it can be formed at room temperature even on any substrate material.

An optical information transmission system according to a seventh aspect of the present invention is an optical information transmission system causing a light wave with a wavelength of 800 nm or more to propagate through an optical element, the optical element including a compact, the compact being formed by subjecting an ultrafine particle brittle material supplied on a substrate to mechanical impact force as a load, whereby the ultrafine particle brittle material is crushed and joined to each other, manganese being added into the ultrafine particle brittle material.

By setting the wavelength of light that propagates through the compact constituting the optical information transmission system to 800 nm or more, a scattering center radius of the light in the compact can be made sufficiently smaller than the wavelength of the light. Therefore, it is possible to obtain an optical information transmission system with small waveguide loss.

An optical information transmission system according to an eighth aspect of the present invention is an optical information transmission system causing a light wave with a wavelength of 800 nm or more to propagate through an integrated optics device in which an optical element including a compact and at least one of optical elements, such as a laser, an electrical-optical converter, an optical-electrical converter, an optical amplifier, an optical waveguide, an optical filter or the like, are integrated on a substrate, the compact being formed by subjecting an ultrafine particle brittle material supplied on the substrate to mechanical impact force as a load, whereby the ultrafine particle brittle material is crushed and joined to each other, manganese being added into the ultrafine particle brittle material.

By setting the wavelength of light that propagates through the compact constituting the optical information transmission system to 800 nm or more, a scattering center radius of the light in the compact can be made sufficiently smaller than the wavelength of the light. Therefore, it is possible to obtain an optical information transmission system with small waveguide loss.

An optical information transmission system according to a ninth aspect of the present invention is an optical information transmission system causing a light wave with a wavelength of 800 nm or more to propagate through an integrated optics device in which an optical element including a compact and at least one of electronic circuits, such as a CPU and a memory, are integrated on a substrate, the compact being formed by subjecting an ultrafine particle brittle material supplied on the substrate to mechanical impact force as a load, whereby the ultrafine particle brittle material is crushed and joined to each other, manganese being added into the ultrafine particle brittle material.

By setting the wavelength of light that propagates through the compact constituting the optical information transmission system to 800 nm or more, a scattering center radius of the light in the compact can be made sufficiently smaller than the wavelength of the light. Therefore, it is possible to obtain an optical information transmission system with small waveguide loss.

An optical element according to a tenth aspect of the present invention is an optical element including a compact, the compact being formed by subjecting an ultrafine particle brittle material supplied on a substrate to mechanical impact force as a load, whereby the ultrafine particle brittle material is crushed and joined to each other, manganese being added into the ultrafine particle brittle material, wherein an average radius d (nm) in a portion (pore (hole), heterogenous phase and the like) contained in the compact and having an index of refraction different from that of a main formation of the compact and a wavelength λ (nm) of light that propagates through the compact have a relationship of $d^6/\lambda^4 < 4 \times 10^{-5}$ ($nm^2$), and wherein an average radius D (nm) of the main formation of the compact and the wavelength λ (nm) of light that propagates through the compact have a relationship of $D^6/\lambda^4 < 4 \times 10^{-5}$ ($nm^2$).

This is based on a finding that a transparent formation can be obtained in the case where even in a material having optical anisotropy a particle size of the formation is sufficiently smaller than the wavelength and there is a relationship of $D^6/\lambda^4 < 4 \times 10^{-5}$ ($nm^2$) between the average radius D (nm) and the wavelength λ (nm) of light that propagates through the compact.

An optical element, an integrated optics device and an optical information transmission system according to an eleventh aspect of the present invention are ones in which the ultrafine particle brittle material is an optoelectronics material. This allows an active element such as an optical modulator, a device and a system using it.

An optical element, an integrated optics device and an optical information transmission system according to a twelfth aspect of the present invention are ones in which lead zirconate titanate or lead zirconate titanate to which lanthanum is added is a principal element in the optoelectronics material as the ultrafine particle brittle material used in them. This allows an active element such as a small-sized optical modulator driven with low voltage, a device and a system using it.

As described above, according to the present invention, it is possible to provide an optical element, an integrated optics device and an optical information transmission system in which transparency of a compact formed by subjecting an ultrafine particle brittle material to mechanical impact force as a load, whereby the ultrafine particle brittle material is crushed, is heightened by adding manganese to the ultrafine particle brittle material, and optical absorption is thereby reduced.

BEST MODE FOR CARRYING OUT THE INVENTION

In order to cause a compact formed by subjecting an ultrafine particle brittle material to mechanical impact force as a load, whereby the ultrafine particle brittle material is crushed and joined to each other, to be usable as an optical element, a large number of experiments have been carried out, and as a result of assiduous examinations, creation of an element with higher transparency than that of conventional one was achieved with success by adding manganese to the ultrafine particle brittle material.

Hereinafter, the present invention including principles of the present invention will be described in Example 1 in detail.

EXAMPLE 1

Figure 2:
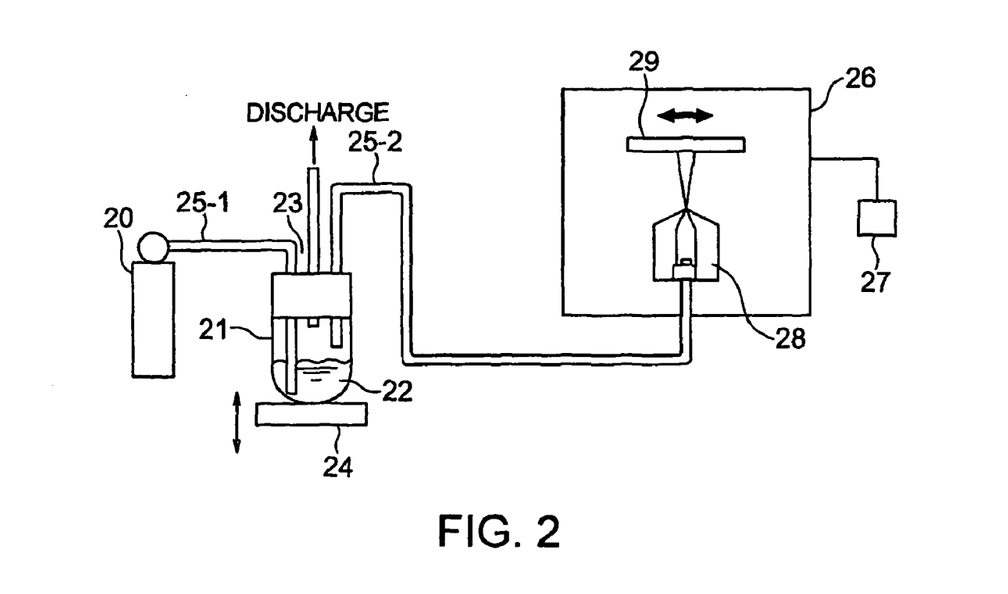
FIG. 2 is a view showing a schematic configuration of a film formation apparatus according to Example 1 of the present invention.

FIG. 2 is a schematic view of a film formation apparatus used in the present invention. A gas cylinder 20 filled with an oxygen gas is connected to a glass bottle 21 via a carrier pipe 25-1. The glass bottle 21 is provided on an agitator 24, and is connected to a vacuum discharge apparatus (not shown in the drawings) through a discharge pipe 23. Further, the glass bottle 21 is also connected to a film formation chamber 26 via a carrier pipe 25-2. The film formation chamber 26 is connected to a vacuum pump 27. Further, the film formation chamber 26 is equipped with a nozzle 28 therein. The nozzle 28 is coupled to the carrier pipe 25-2.

Film formation is carried out as follows.

Namely, a powder raw material (ultrafine particle brittle material) 22 is put in the glass bottle 21. Then, after discharging air from the glass bottle 21 to a vacuum of about 20 Torr via the discharge pipe 23, oxygen as a carrier gas is introduced from the gas cylinder 20 while controlling a flow rate. By vibrating the glass bottle 21 by the agitator 24 while introducing oxygen, aerosol in which minute particles of raw powder are dispersed in the air is generated.

The air is discharged from the film formation chamber 26 to a desired degree of vacuum by the vacuum pump 27, whereby a difference between pressure in the inside of the glass bottle 21 and pressure in the inside of the film formation chamber 26 is generated. This pressure difference conveys the aerosol generated in the glass pipe 21 into the film formation chamber 26 via the carrier pipe 25-2. The aerosol conveyed into the film formation chamber 26 is accelerated by passing through the nozzle 28 to impact against a substrate 29. As a result, the substrate 29 is sprayed with the raw powder to form a thin film thereon.

Film formation conditions of a plurality of samples according to the present invention and a plurality of comparative samples are as follows.

Namely, the carrier gas is oxygen, an angle made by the nozzle and the substrate (an angle of incidence) is 10 degrees, the amount of flowing gas is 12 liter/minute, film formation speed is 0.5 μm/minute, and the frequency of vibration of the agitator is 250 rpm. Glass was used as the substrate. Six kinds of lead zirconate titanate (PZT) type power each of which is oxide having a high electro-optical effect were used as a film formation material. Composition of PZT is $Pb(Zr_xTi_{1-x})O_3$ (where x=0.3, 0.45 or 0.6), and Mn is added or not added to each composition. One to which Mn is added is a sample according to the present invention, while one to which Mn is not added is a comparative sample. An additive amount of Mn is 0.5 at %. An average particle size of the raw powder is set to 0.7 μm. PZT type powder of the film formation material is composition of a ferroelectric substance having a perovskite type crystal structure, and is composition applicable to an optical device having a large primary electro-optical coefficient.

Figure 1:
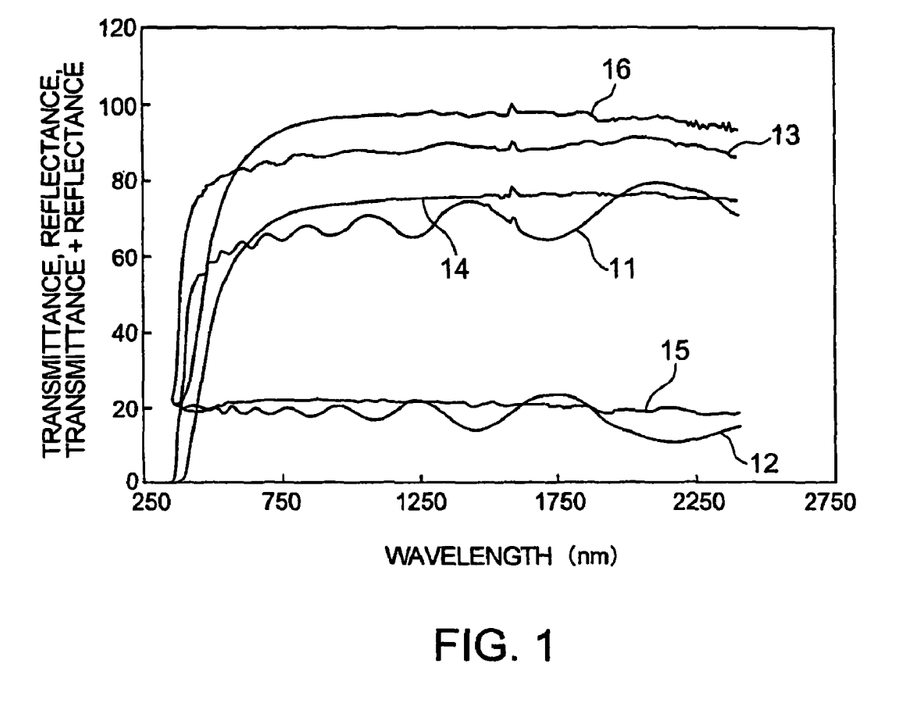
FIG. 1 is a view showing transmittance, reflectance, and transmittance+reflectance spectra of each of a sample in which Mn is added into $Pb(Zr_{0.3}Ti_{0.7})O_3$ according to Example 1 of the present invention and a sample in which Mn is not added.

FIG. 1 shows transmittance, reflectance and transmittance+reflectance spectra of samples in which Mn is added or not added to $Pb(Zr_{0.3}Ti_{0.7})O_3$ (hereinafter, respectively indicated as $Pb(Zr_{0.3}Ti_{0.7})O_3$+Mn and $Pb(Zr_{0.3}Ti_{0.7})O_3$). A horizontal axis denotes a wavelength, while a longitudinal axis denotes transmittance, reflectance and transmittance+reflectance. They were measured by a spectrophotometer. A surface of each sample was polished, whereby an influence of surface scattering is eliminated as much as possible. A large-sized integrating sphere was used as a detector, and light scattered by each sample was also measured.

As shown in FIG. 1, transmittance 11 of $Pb(Zr_{0.3}Ti_{0.7})O_3$ is increased while oscillating with the wavelength of 400 nm, which is an absorption edge, or more and is nearly saturated at the wavelength of 1,000 nm or more. This oscillation of the transmittance 11 is caused by optical interference of the thin film formed by the AD method.

Further, reflectance 12 of $Pb(Zr_{0.3}Ti_{0.7})O_3$ is oscillated at the overall wavelength range with the center of nearly 20%.

Transmittance+reflectance 13 of $Pb(Zr_{0.3}Ti_{0.7})O_3$ is about 90% at a range with a wavelength of 1,000 nm or more, which is sufficiently apart from the absorption edge, and this indicates that optical absorption occurs at this wavelength range. It is thought that optical absorption occurred due to film formation by the AD method because no optical absorption occurs at this region in the PZT thin film and the like. In measurement by an X-ray absorption microstructure spectroscopy, large disorder was observed in a local structure of the PZT film formed by the AD method. It is thought that this disorder of the local structure forms a localized level between bands, whereby optical absorption occurs. Since such optical absorption causes large waveguide loss of the optical element, it is required to reduce it as much as possible.

A large number of experiments have been carried out in order to reduce this optical absorption, and as a result of assiduous examinations, creation of an element with higher transparency than that of conventional one was achieved with success by adding manganese to a constituent material. Hereinafter, the effect will be described using FIG. 1. Optical characteristic transmittance 14 and reflectance 15 of $Pb(Zr_{0.3}Ti_{0.7})O_3$+Mn in which Mn is added are respectively increased at the overall wavelength range more than transmittance 11 and reflectance 12 of $Pb(Zr_{0.3}Ti_{0.7})O_3$. Transmittance+reflectance 16 of $Pb(Zr_{0.3}Ti_{0.7})O_3$+Mn is nearly 100% at a range with a wavelength of 1,000 nm or more, which is sufficiently apart from the absorption edge, and optical absorption could be reduced seriously. Manganese is a polyvalent metal, and it is thought that there is an effect to compensate irregular of valency caused by disorder of the local structure. This manganese addition made it possible to dramatically improve large waveguide loss generated in the optical element.

The similar improvement effects of the optical absorption by addition of manganese described above can be obtained by not only $Pb(Zr_{0.3}Ti_{0.7})O_3$+Mn but also other composition.

Figure 3:
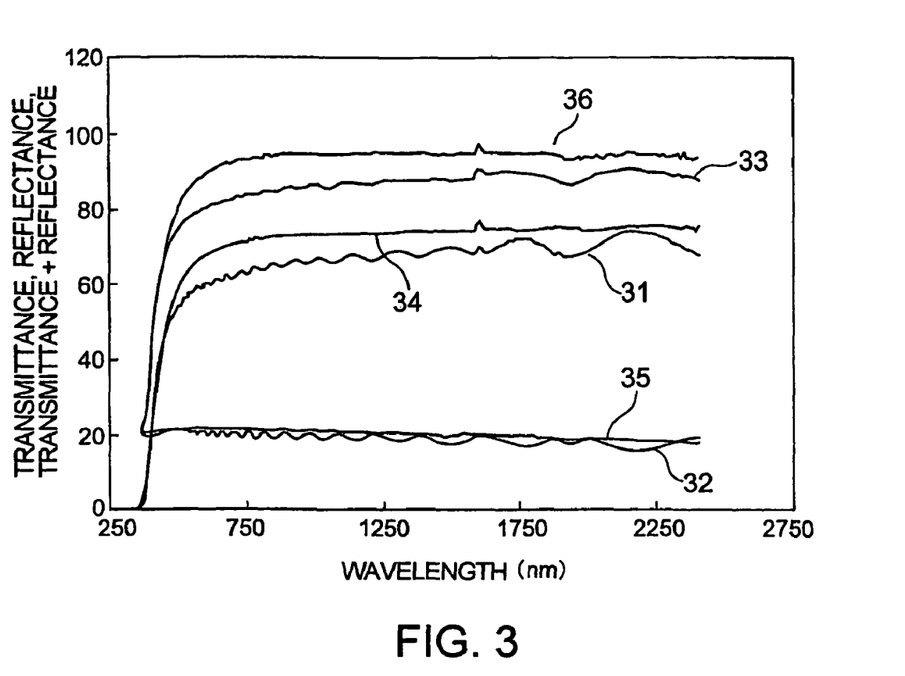
FIG. 3 is a view showing transmittance, reflectance, and transmittance+reflectance spectra of each of a sample in which Mn is added into $Pb(Zr_{0.45}Ti_{0.55})O_3$ according to Example 1 of the present invention and a sample in which Mn is not added.

FIG. 3 shows transmittance, reflectance and transmittance+reflectance spectra of $Pb(Zr_{0.45}Ti_{0.55})O_3$+Mn and $Pb(Zr_{0.45}Ti_{0.55})O_3$. Solid lines 31, 32 and 33 indicate transmittance, reflectance and transmittance+reflectance spectra of $Pb(Zr_{0.45}Ti_{0.55})O_3$, respectively. Solid lines 34, 35 and 36 indicate transmittance, reflectance and transmittance+reflectance spectra of $Pb(Zr_{0.45}Ti_{0.55})O_3$+Mn, respectively. It can be seen that optical absorption generated by $Pb(Zr_{0.45}Ti_{0.55})O_3$ can be inhibited by adding manganese thereto.

Figure 4:
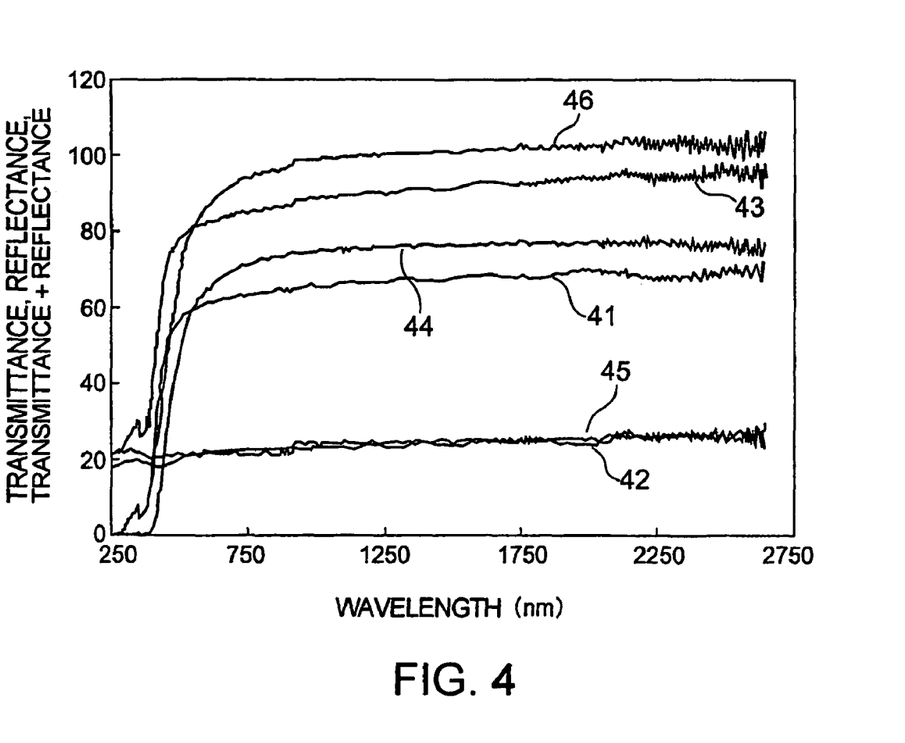
FIG. 4 is a view showing transmittance, reflectance, and transmittance+reflectance spectra of each of a sample in which Mn is added into $Pb(Zr_{0.6}Ti_{0.4})O_3$ according to Example 1 of the present invention and a sample in which Mn is not added.

FIG. 4 shows transmittance, reflectance and transmittance+reflectance spectra of $Pb(Zr_{0.6}Ti_{0.4})O_3$+Mn and $Pb(Zr_{0.6}Ti_{0.4})O_3$. Solid lines 41, 42 and 43 indicate transmittance, reflectance and transmittance+reflectance spectra of $Pb(Zr_{0.6}Ti_{0.4})O_3$, respectively. Solid lines 44, 45 and 46 indicate transmittance, reflectance and transmittance+reflectance spectra of $Pb(Zr_{0.6}Ti_{0.4})O_3$+Mn, respectively. It can be seen that optical absorption generated by $Pb(Zr_{0.6}Ti_{0.4})O_3$ can be resolved by adding manganese thereto.

The present Example relates to a PZT that is an optoelectronics material, but a material system is not limited thereto. Optoelectronics materials, such as lead zirconate titanate to which lanthanum is added, barium titanate, strontium added barium titanate and KTN, and optical waveguide forming materials such as $SiO_2$ and silicon nitride also have the similar effect. Further, a material system in which other element is added to any one of optoelectronics materials such as PZT, lead zirconate titanate to which lanthanum is added, barium titanate, strontium added barium titanate, KTN and optical waveguide forming materials such as $SiO_2$ and silicon nitride also has the similar effect.

EXAMPLE 2

In the present Example, a reduction method of light scattered by an optical element formed by using a PZT type pulverized material in which manganese is added to an ultrafine particle brittle material and forming a thin film by an AD method will be described. A film formation apparatus is the same as that in Example 1. The carrier gas is oxygen, the amount of flowing gas is 12 liter/minutes, film formation speed is 0.5 μm/minutes, and the frequency of vibration of an agitator is 250 rpm. An angle made by a nozzle and a substrate (an angle of incidence) was changed among 0, 5 and 10 degrees. Glass was used as the substrate. $Pb(Zr_{0.3}Ti_{0.7})O_3$+Mn was used as raw powder.

Figure 5:
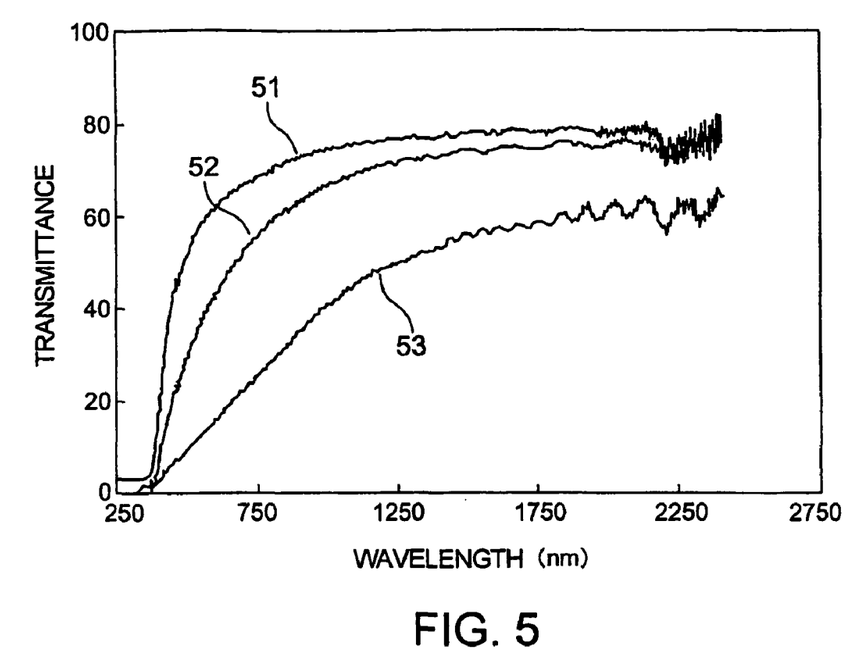
FIG. 5 is a view showing transmittance, reflectance, and transmittance+reflectance spectra each of three samples in which Mn is added or not added into $Pb(Zr_{0.3}Ti_{0.7})O_3$ according to Example 2 of the present invention and a film formation condition is different from each other.

FIG. 5 shows transmittance spectra of samples in the case where an angle of incidence is set to each of 0, 5 and 10 degrees. A surface of each sample was polished, whereby an influence of surface scattering is eliminated as much as possible. In a spectrophotometer, an absolute reflectance measurement system in which a detector is apart from each sample by 10 cm or more was used as a detection system. This makes it possible to efficiently detect decrease of the transmittance due to the scattered light of the sample.

In view of FIG. 5, transmittance 51 of the sample in the case where an angle of incidence is 10 degrees is increased together with a wavelength of 400 nm, which is an absorption edge, or more and is nearly saturated at the wavelength of 1,000 nm or more. On the other hand, both transmittance 52 of the sample and transmittance 53 of the sample in the case where angles of incidence are respectively 5 degrees and 0 degree are not saturated even at the wavelength of 1,000 nm.

Causes of this difference of the transmittance between the samples can be explained using the Rayleigh scattering theory by a difference between pore (hole) radii, presence or absence of phases having different compositions (heterogenous phase), and a difference of particle sizes in constituent minute particles having optical anisotropy. Therefore, in order to make an extinction coefficient β smaller, it is effective to make a wavelength λ of light to be used larger; to make a scattering center radius d smaller; to make a difference M of indices of refraction between scatterers and media smaller; and to make a particle size D of the constituent minute particle smaller. Namely, if the scattering center radius d and the particle size D of the constituent minute particle can be made sufficiently smaller compared with the wavelength λ, an optical element can be caused to be practicably transparent. A range of $d^6/\lambda^4$ acquired experimentally is $4 \times 10^{-5}$ nm$^2$ or less, and it is desired that the range of $d^6/\lambda^4$ is $1 \times 10^{-5}$ nm$^2$ or less, and a range of $D^6/\lambda^4$ becomes $D^6/\lambda^4 < 4 \times 10^{-5}$ nm$^2$.

Further, in an optical information transmission system using the optical element formed by the present system, there is a lower limit in the usable wavelength of light. In order to control transmission loss to a practicable level in an optical information transmission system using the optical element by this film formation method, a wavelength of light used to transmit information is required to be 800 nm or more.

EXAMPLE 3

Next, Example of an optical modulator using the present optical element will be described. First, an ITO film of 180 nm was formed on a glass substrate as a lower electrode by means of a sputtering method. A magnetron sputtering method was used, and the film was formed by means of argon gas at room temperature.

Resist for lift-off was formed on the ITO lower electrode in the form of a Mach-Zehnder type waveguide. Subsequently, a film of $Pb(Zr_{0.3}Ti_{0.7})O_3$+Mn was formed with 2 μm to become a core layer. Film formation conditions were the same as those in Example 1. Subsequently, the resist was removed, and the surface of $Pb(Zr_{0.3}Ti_{0.7})O_3$+Mn was flattened by polishing to make a waveguide. Next, a film of PLZT+Mn whose index of refraction was made smaller was formed with 2.5 μm by the present system, and was polished until the thickness becomes 2.0 μm to become a cladding layer. An ITO electrode and an Au electrode were formed on a core layer by means of a sputtering method to become an upper electrode.

Light with a wavelength of 1.55 μm was introduced to the formed optical modulator by a lensed optical fiber, and voltage of 10V was applied to the electrodes, whereby the degree of modulation of 12 dB can be obtained.

When wavelength dependency of propagation loss of the optical modulator in the present Example was measured, waveguide loss became 15 dB or less at a wavelength of 800 nm or more, and it was applicable. Moreover, the waveguide loss was lowered as the measured wavelength was heightened, and it became 2 dB at a wavelength of 1.55 μm.

In the present Example, a lift-off method was used to make a $Pb(Zr_{0.3}Ti_{0.7})O_3$+Mn core layer. However, it can be formed by a method of forming a core layer; forming a desired waveguide shape by means of resist; and subjecting the layer to etching such as reactive ion etching. Further, by changing the waveguide shape of the present Example, an optical switch can be formed.

Since a property of the optical element according to the present invention does not depend on a substrate material, it has effectiveness that it can be formed on a polycrystalline substance having a different crystal structure, such as an ITO film.

Further, since the optical element of the present invention can be formed regardless of a substrate and a foundation layer, the optical element is formed on a substrate on which an optical element, such as a laser, an electrical-optical converter, an optical-electrical converter, an optical amplifier, an optical waveguide and an optical filter, is formed in advance, or on a substrate on which an electronic circuit, such as a CPU and a memory, is formed, whereby an integrated optics device can be made.

EXAMPLE 4

Figure 6:
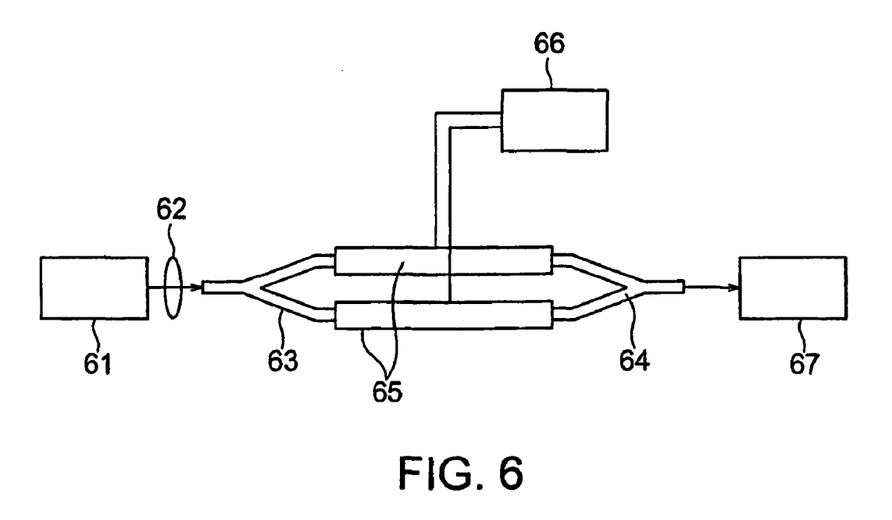
FIG. 6 is a view showing a schematic configuration of an optical information transmission system according to Example 4 of the present invention.

FIG. 6 is a block diagram of an optical information transmission system of Example 4. Continuous light outputted from a laser 61 is condensed at a microlens 62, and enters an optical modulator 63. The optical modulator 63 is formed from a Mach-Zehnder type waveguide 64, which is formed in the same process as that in Example 3, and electrodes 65, and the optical modulator 63 is formed on a substrate on which the laser is formed in advance. The electrodes 65 are electrically connected to a modulating signal generating circuit 66 to receive supply of high frequency signals. As a result, the optical modulator 63 is driven with voltage. The index of refraction of the waveguide changes depending on this voltage, and this makes it possible to modulate an optical signal. The optical signal modulated by the optical modulator is converted into an electric signal by an optical-electrical converter 67.

When wavelength dependency of S/N was measured by inputting a signal of 100 MHz to the optical information transmission system of the present Example, the S/N became 20 dB or more at a wavelength of 800 nm or more, and it was applicable.

The invention claimed is:

1. An optical element comprising a compact, the compact being formed by subjecting an ultrafine particle brittle material supplied on a substrate to mechanical impact force as a load, whereby the ultrafine particle brittle material is crushed and joined to each other, wherein manganese is added into the ultrafine particle brittle material, and an average radius d (nm) in a portion contained in the compact and having an index of refraction different from that of a main formation of the compact and a wavelength λ (nm) of light that propagates through the compact have a relationship of $d^6/\lambda^4 < 4 \times 10^{-5}$ $(nm^2)$.

2. The optical element as claimed in claim 1, wherein the ultrafine particle brittle material comprises an optoelectronics material.

3. The optical element as claimed in claim 2, wherein in the optoelectronics material, lead zirconate titanate or lead zirconate titanate to which lanthanum is added is a principal element.

4. An optical element comprising a compact, the compact being formed by subjecting an ultrafine particle brittle material supplied on a substrate to mechanical impact force as a load, whereby the ultrafine particle brittle material is crushed and joined to each other, wherein manganese is added into the ultrafine particle brittle material, and an average radius d (nm) in a portion contained in the compact and having an index of refraction different from that of a main formation of the compact and a wavelength λ (nm) of light that propagates through the compact have a relationship of $d^6/\lambda^4 < 1 \times 10^{-5}$ $(nm^2)$.

5. The optical element as claimed in claim 1, wherein the optical element is constructed from a lower electrode formed on the substrate, a waveguide formed on the lower electrode and made of the compact, and an upper electrode formed on the waveguide.

6. An integrated optics device in which a first optical element including a compact and a second optical element different from the first optical element are integrated on a substrate, the compact being formed by subjecting an ultrafine particle brittle material supplied on the substrate to mechanical impact force as a load, whereby the ultrafine particle brittle material is crushed and joined to each other, wherein manganese is added into the ultrafine particle brittle material, and an average radius d (nm) in a portion contained in the compact and having an index of refraction different from that of a main formation of the compact and a wavelength λ (nm) of light that propagates through the compact have a relationship of $d^6/\lambda^4 < 4 \times 10^{-5}$ $(nm^2)$.

7. The integrated optics device as claimed in claim 6, wherein the second optical element comprises a laser, an electrical-optical converter, an optical-electrical converter, an optical amplifier, an optical waveguide or an optical filter.

8. The integrated optics device as claimed in any one of claims 6, wherein the ultrafine particle brittle material comprises an optoelectronics material.

9. The integrated optics device as claimed in claim 8, wherein in the optoelectronics material, lead zirconate titanate or lead zirconate titanate to which lanthanum is added is a principal element.

10. An integrated optics device in which an optical element including a compact and an electronic circuit are integrated on a substrate, the compact being formed by subjecting an ultrafine particle brittle material supplied on the substrate to mechanical impact force as a load, whereby the ultrafine particle brittle material is crushed and joined to each other, wherein manganese is added into the ultrafine particle brittle material, and an average radius d (nm) in a portion contained in the compact and having an index of refraction different from that of a main formation of the compact and a wavelength λ (nm) of light that propagates through the compact have a relationship of $d^6/\lambda^4 < 4 \times 10^{-5}$ $(nm^2)$.

11. The integrated optics device as claimed in claim 10, wherein the electronic circuit comprises a central processing unit or a memory.

12. An optical information transmission system causing a light wave with a wavelength of 800 nm or more to propagate through an integrated optics device in which a first optical element including a compact and a second optical element different from the first optical element are integrated on a substrate, the compact being formed by subjecting an ultrafine particle brittle material supplied on the substrate to mechanical impact force as a load, whereby the ultrafine particle brittle material is crushed and joined to each other, manganese being added into the ultrafine particle brittle material.

13. The optical information transmission system as claimed in claim 12, wherein the second optical element comprises a laser, an electrical-optical converter, an optical-electrical converter, an optical amplifier, an optical waveguide or an optical filter.

14. The optical information transmission system as claimed in claim 12, wherein the ultrafine particle brittle material comprises an optoelectronics material.

15. The optical information transmission system as claimed in claim 14, wherein in the optoelectronics material, lead zirconate titanate or lead zirconate titanate to which lanthanum is added is a principal element.

16. An optical information transmission system causing a light wave with a wavelength of 800 nm or more to propagate through an optical element, the optical element including a compact, the compact being formed by subjecting an ultrafine particle brittle material supplied on a substrate to mechanical impact force as a load, whereby the ultrafine particle brittle material is crushed and joined to each other, manganese being added into the ultrafine particle brittle material.

17. An optical information transmission system causing a light wave with a wavelength of 800 nm or more to propagate through an integrated optics device in which an optical element including a compact and an electronic circuit are integrated on a substrate, the compact being formed by subjecting an ultrafine particle brittle material supplied on the substrate to mechanical impact force as a load, whereby the ultrafine particle brittle material is crushed and joined to each other, manganese being added into the ultrafine particle brittle material.

18. The optical information transmission system as claimed in claim 17, wherein the electronic circuit comprises a central processing unit or a memory.

19. An optical element comprising a compact, the compact being formed by subjecting an ultrafine particle brittle material supplied on a substrate to mechanical impact force as a load, whereby the ultrafine particle brittle material is crushed and joined to each other, manganese being added into the ultrafine particle brittle material, wherein an average radius d (nm) in a portion contained in the compact and having an index of refraction different from that of a main formation of the compact and a wavelength $\lambda$ (nm) of light that propagates through the compact have a relationship of $d^6/\lambda^4 < 4 \times 10^{-5}$ ($nm^2$), and wherein an average radius D (nm) of the main formation of the compact and the wavelength $\lambda$ (nm) of light that propagates through the compact have a relationship of $D^6/\lambda^4 < 4 \times 10^{-5}$ ($nm^2$).

* * * * *